Figure 1:
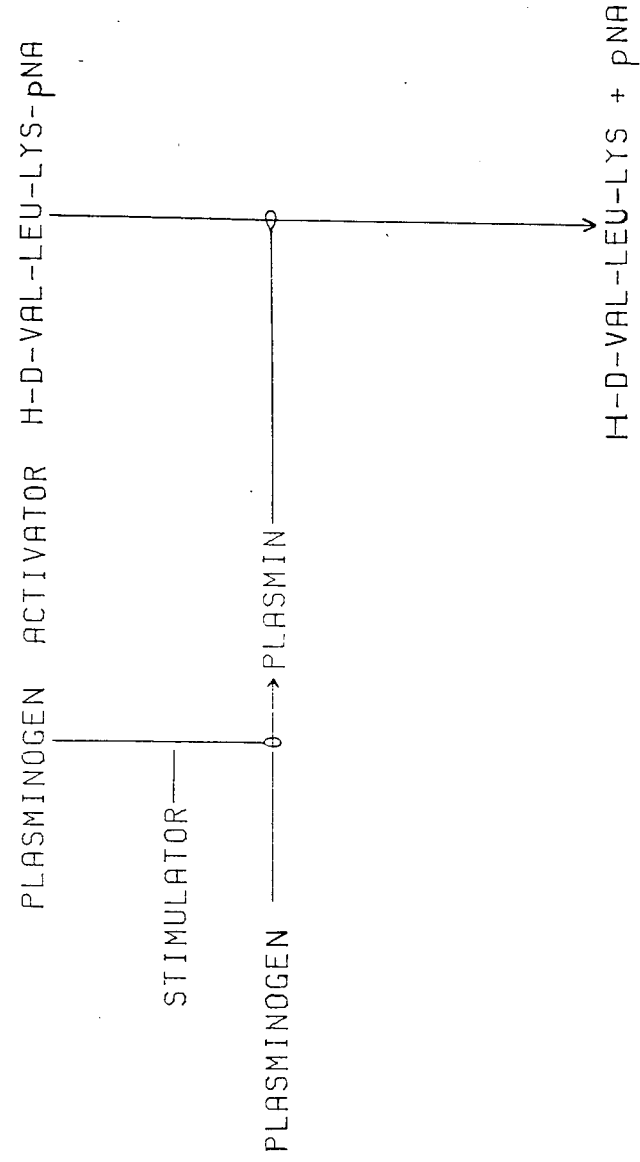

United States Patent [19]

Verheijen et al.

[11] Patent Number: 4,563,420

[45] Date of Patent: Jan. 7, 1986

[54] PROCESS FOR ASSAYING THE ACTIVITY OF TISSUE PLASMINOGEN ACTIVATOR, AND KIT SUITABLE FOR USE IN SAID PROCESS

[75] Inventors: Johan H. Verheijen, Rotterdam; Willem Nieuwenhuizen, Bunnik, both of Netherlands

[73] Assignee: Nederlandse Centrale Organisatie Voor Toegepast-Natuurwetenschappelijk Onderzoek, The Hague, Netherlands

[21] Appl. No.: 492,494

[22] Filed: May 6, 1983

[30] Foreign Application Priority Data

May 13, 1982 [NL] Netherlands ............ 8201987

[51] Int. Cl.[4] ............................................. C12Q 1/56
[52] U.S. Cl. ............................................. 435/13
[58] Field of Search ................................... 435/13

[56] References Cited

U.S. PATENT DOCUMENTS 4,011,142  3/1977  Jacobi ...................... 435/13
4,278,762  7/1981  Svendsen ................... 435/13

Primary Examiner—Sam Rosen
Attorney, Agent, or Firm—Brumbaugh, Graves, Donohue & Raymond

[57] ABSTRACT

The invention relates to a process for assaying the activity of tissue plasminogen activator (TA), in which a sample is incubated with plasminogen, a substrate for plasmin giving a detectable reaction product on reaction with plasmin, preferably H-D-Val-Leu-Lys-pNA, and, as a stimulator for the conversion of plasminogen to plasmin by TA, water-soluble fibrinogen or fibrin fragments comprising at least partially the D-domains of the fibrinogen or fibrin molecule. The amount of the detectable reaction product of the plasmin substrate is measured. Preferably, said fibrinogen or fibrin fragments have been obtained by reacting fibrinogen or fibrin with CNBr and removing lower molecular components from the reaction product.

The invention also relates to kits for performing the assay and comprising the reagents to be used.

14 Claims, 13 Drawing Figures

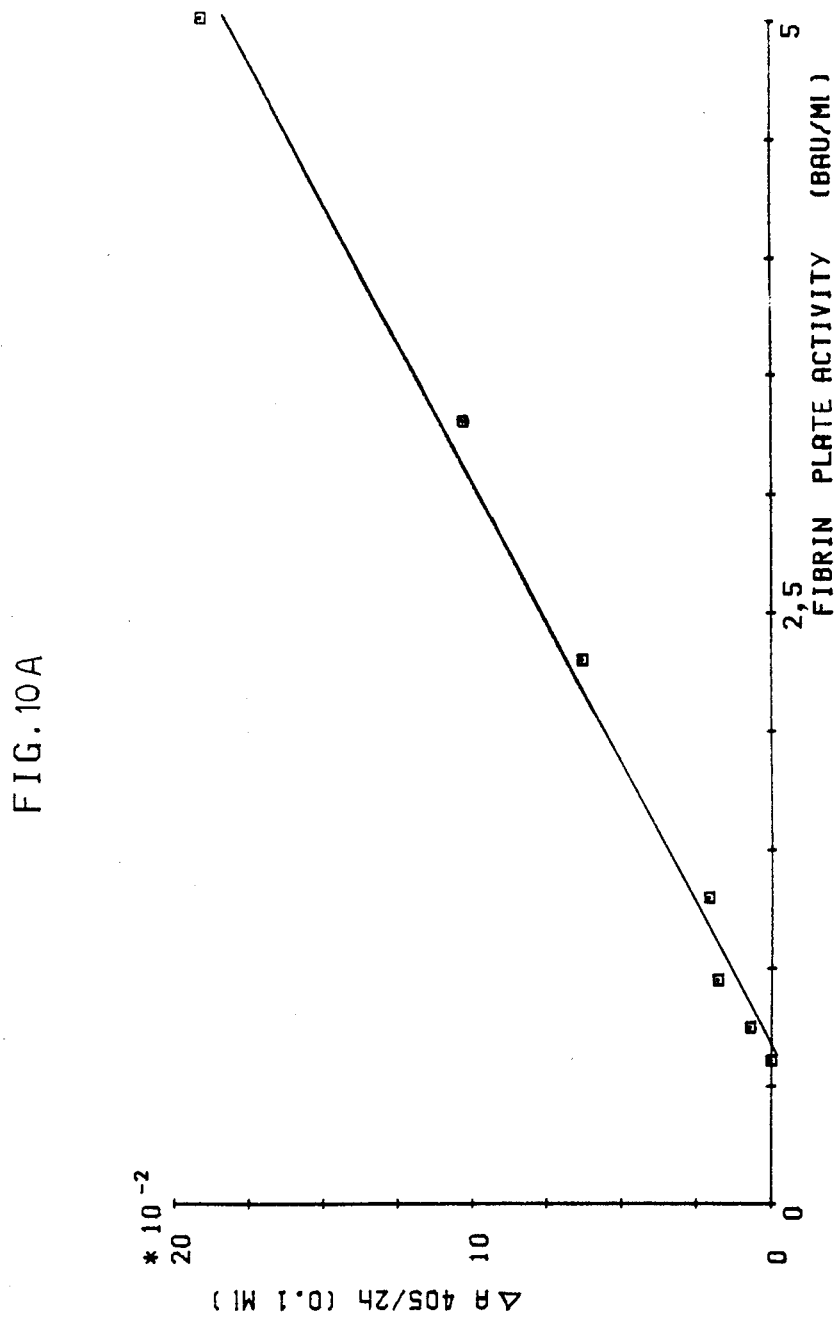

PROCESS FOR ASSAYING THE ACTIVITY OF TISSUE PLASMINOGEN ACTIVATOR, AND KIT SUITABLE FOR USE IN SAID PROCESS

The present invention relates to a process for assaying the activity of tissue plasminogen activator in a sample, in which a sample is incubated with plasminogen, a stimulator for the conversion of plasminogen to plasmin by tissue plasminogen activator, as well as a plasmin substrate giving a detectable reaction product on reaction with plasmin. Further, the invention relates to a kit comprising containers in which reagents suitable for carrying out this process are present.

Plasminogen activators catalyze the conversion of plasminogen to plasmin. Plasmin is capable of lysing blood clots by degrading the fibrin present therein. Various plasminogen activators are known, the most important of which are urokinase (UK) and tissue type plasminogen activator (TA). In particular, TA seems to be involved in fibrinolysis in vivo, most probably as a result of its specific affinity for fibrin. Therefore, there is a great need of a reliable and simple method for estimating the activity of TA in body fluids, especially in plasma, of healthy people and of patients having certain disorders, such as recurrent thrombosis or unexplained bleedings.

Three different types of TA assays may be distinguished, namely immunological assays, direct functional assays and indirect functional assays. In immunological assays the presence of plasminogen activator antigen is detected, but these methods do not give information about the activity of the enzyme. In direct functional assays the hydrolysis of a substrate, for example (labelled) plasminogen or a synthetic chromogenic or fluorogenic peptide substrate, by plasminogen activator is measured. In the indirect functional assays plasminogen is converted to plasmin under the influence of the plasminogen activator, and the amount of plasmin formed is assayed by using a plasmin substrate. The two reactions involved, namely the activation of plasminogen and the hydrolysis of the substrate, may be carried out simultaneously or consecutively. Important examples of the indirect functional assay are the fibrin plate method and the various methods in which the time necessary for fibrin clot lysis is measured. In all of these methods the natural plasmin substrate, namely fibrin, is used. A sensitive immunological assay for TA is not available presently. The direct functional assays are not sufficiently sensitive or are cumbersome. Several sensitive indirect assays are available. The fibrin plate method and the clot lysis time method have the disadvantage that the course of the reactions involved is kinetically unclear. This is why the interpretation of the results obtained with these methods, especially when inhibiting substances are present, as is the case in plasma, is difficult.

The present invention relates to an indirect assay method for the activity of plasminogen activator of the tissue type in a sample, in which a sample is incubated with plasminogen, a stimulator for the conversion of plasminogen to plasmin by tissue plasminogen activator, as well as a plasmin substrate giving a detectable reaction product on reaction with plasmin.

Such a method is described by M. Ranby and P. Wallén in Progress in Fibrinolysis Vol. V, Editors; J. F. Davidson, J. M. Nilsson, B. Astedt; Churchill Livingstone, Edinburgh 1981. In this method a sample in which the activity of TA is to be assayed, is incubated with plasminogen. The plasmin formed catalyzes the hydrolysis of the peptide substrate H-D-Val-Leu-Lys-pNA, thereby liberating the coloured compound, p-nitroaniline (pNA). The formation of this compound can be measured spectrophotometrically. The principle of this method is indicated schematically in FIG. 1. Ranby and Wallén use fibrin monomer as a stimulator for the conversion of plasminogen to plasmin by tissue plasminogen activator. This results in a very high increase of the rate of the plasmin formation. A disadvantage of this method is, however, that fibrin monomer is sparingly soluble, which complicates the method, among others by turbidity. Namely, the mixture has to be filtered after the incubation and then the spectrophotometric estimation can be carried out.

It was found that the disadvantage of the low solubility of fibrin monomer in the known assay method can be avoided by using water-soluble fibrinogen or fibrin fragments comprising at least partially the D-domains of the molecule and being smaller than fragment X as a stimulator for the conversion of plasminogen to plasmin under the influence of tissue plasminogen activator.

Water-soluble fibrinogen and fibrin fragments comprising at least partially the D-domains of the fibrinogen or fibrin molecule and being smaller than fragment X, are known. They may be obtained by enzymatic, chemical or mechanical degradation or fragmentation of fibrinogen or fibrin.

The enzymatic (proteolytic) degradation of fibrin or of fibrinogen is normally carried out with plasmin. This degradation proceeds via a number of intermediate products. First, fragments X are formed which, in comparison with fibrinogen, lack important parts of the C-terminal ends of the Aα-chains. Then fragment X is split into a fragment Y and a fragment D, and then fragment Y is in turn split into a fragment D and a fragment E. The D-fragments originate from the midchain and C-terminal regions of the fibrinogen molecule, and E-fragments consist of remnants of the N-terminal regions of all of the six fibrinogen chains. The homogeneity, structure and the properties of the D-fragments depend on the media in which the degradation with plasmin is carried out. For example, the degradation in the presence of calcium ions yield homogeneous D-fragments which are called D-cate-fragments and which contain an intact C-terminal end of the γ-chain [Tromb. Res. 10, 803–812 (1977)]. In the presence of EGTA or similar compounds another D-fragment is formed which is called D EGTA. In comparison with D-cate, this fragment lacks a part having a molecular weight of 13,000, at the C-terminal end of its γ-chain remnant [Biochim. Biophys. Acta 667, 321–327 (1981)]. Cross-linked fibrin on splitting with plasmin in media containing calcium ions yields D-dimer-fragments plus an E-fragment [J. Biol. Chem. 248, 4584–4590 (1973)]. The D-dimer can be considered as consisting of two D-cate-fragments isopeptide-bonded via the C-terminal parts of their γ-chains.

Among the fragments obtained by the enzymatic degradation of fibrin or fibrinogen, any of the stimulating fragments may be used in the present assay method provided the fragments comprise at least partially the D-domains of the molecule and are smaller than fragment X. Although fragment X comprises the D-domains of the fibrin(ogen) molecule, fragment X was found to exert hardly any stimulating activity on the conversion of plasminogen to plasmin under the influence of tissue plasminogen activator. Fragment Y and the D-fragments D EGTA and D-dimer are excellently, and D-cate somewhat less suitable as stimulators. Fragment Y is most preferred. D-dimer does not provoke maximum stimulation because D-dimer not only has a stimulating activity on the conversion of plasminogen to plasmin by TA, but also has an inhibiting influence on the proteolytic activity of plasmin. The other fragments mentioned do not possess this property. E-fragments are not suitable for the present assay method because they do not show the desired stimulating activity.

A known chemical method for the degradation of fibrin or fibrinogen is a treatment with CNBr.

The degradation of fibrinogen with CNBr is described, for example, by B. Blombäck et al. in Nature 218 (1968), pages 130–134. This degradation was carried out in connection with the elucidation of the structure of fibrinogen. According to this method a 1% fibrinogen solution in 70% formic acid is dialysed over/night at 5° C. against 70% formic acid. Then 1.3 g of CNBr per 100 ml of solution is added and the solution left for 20-25 hours at room temperature. The fragments obtained by degradation with CNBr are, without further separation, excellently useful as stimulators in the present assay method. If desired, the mixtures may be resolved into the separate fragments and the active fragments comprising at least partially the D-domains of the fibrin(ogen) molecule may be used in the present assay method. It is preferred, however, to use the fragment mixtures obtained by reaction with CNBr as such, thereby avoiding the time-consuming separation. It was found that use of the mixture of fragments obtained as such by reaction with CNBr gives completely reproduceable results. It is desirable to remove from the reaction product of the CNBr treatment the reagents used and any low molecular products, for example salts and sugars which may be present in the fibrinogen preparation for stabilisation purposes. This is accomplished most easily by dialysis against distilled water using a cellophane membrane allowing passage of compounds having a molecular weight of about 10,000. The solution of the fragments obtained after the dialysis may be lyophilized or may be stored as a solution in frozen condition.

The preparation of the fragments by reaction with CNBr may be carried out with fibrin with the same good result.

The plasminogen used in the present method should be as pure as possible and, in particular, should contain the lowest possible amount of plasmin, because the latter, like the plasmin formed under the influence of the activator (TA), will react with the substrate.

As a plasmin substrate giving a detectable reaction product on reaction with plasmin, the above-mentioned H-D-Val-Leu-Lys-pNA is preferred, although other peptide substrates, such as H-Val-cyclohexylalanine-Arg-pNA may be used as well. In general, suitable substrates are those in which the amino acid to which the p-nitroaniline or another chromogenic or fluorogenic group is attached, is Lys or Arg, and wherein the amino acid attached to the Lys or Arg is an apolar amino acid.

In the following, the term fibrinogen fragments will also refer to the corresponding fibrin fragments.

Figure 5:
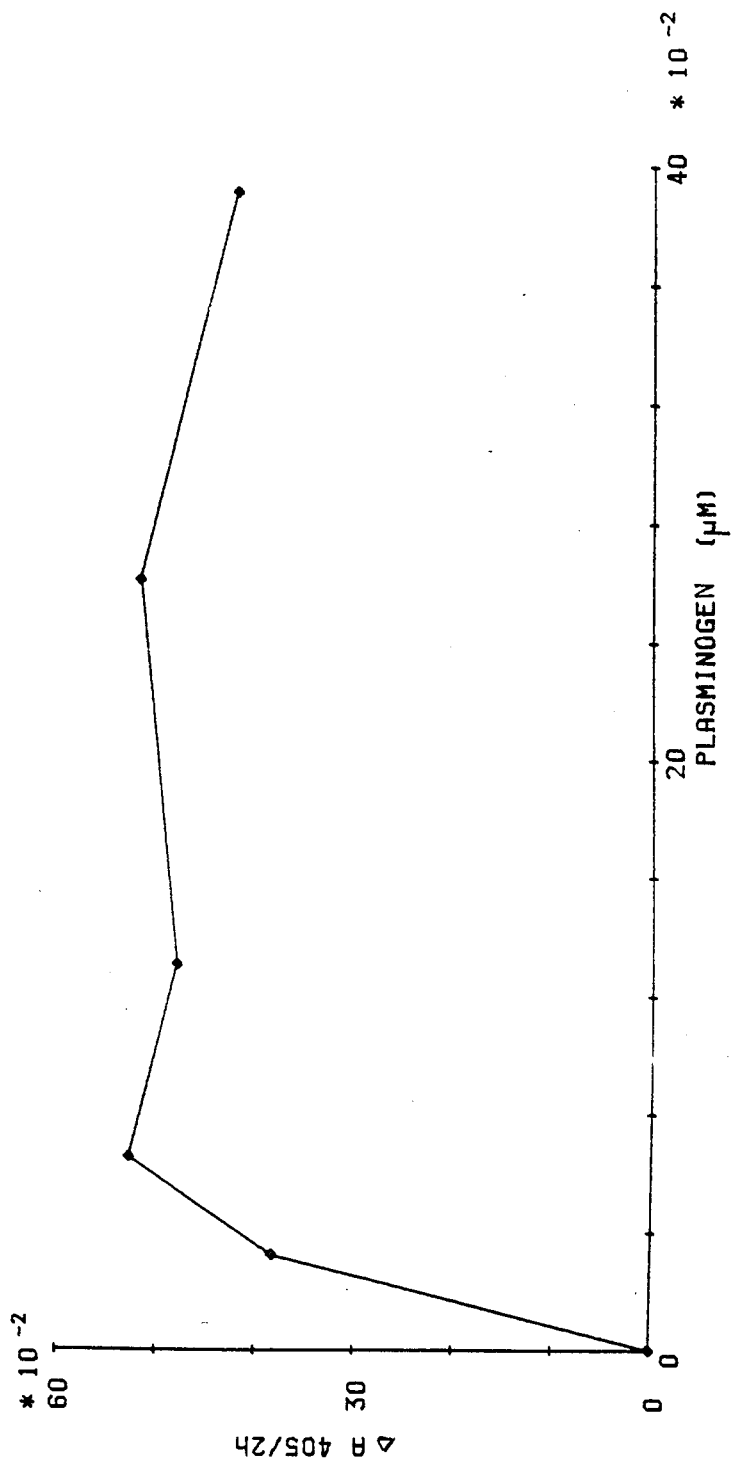

Tests have shown that the plasminogen as well as the fibrinogen fragments have to be present in a certain minimum concentration in order to obtain good correlation between the amount of plasmin formed (and, consequently, of p-nitroaniline) and the amount of TA present. Thus, the fibrinogen fragments should be present in a concentration of at least 120 µg/ml (see FIG. 2) and the plasminogen concentration should be at least 0.06 µM (FIG. 5).

Figure 3:
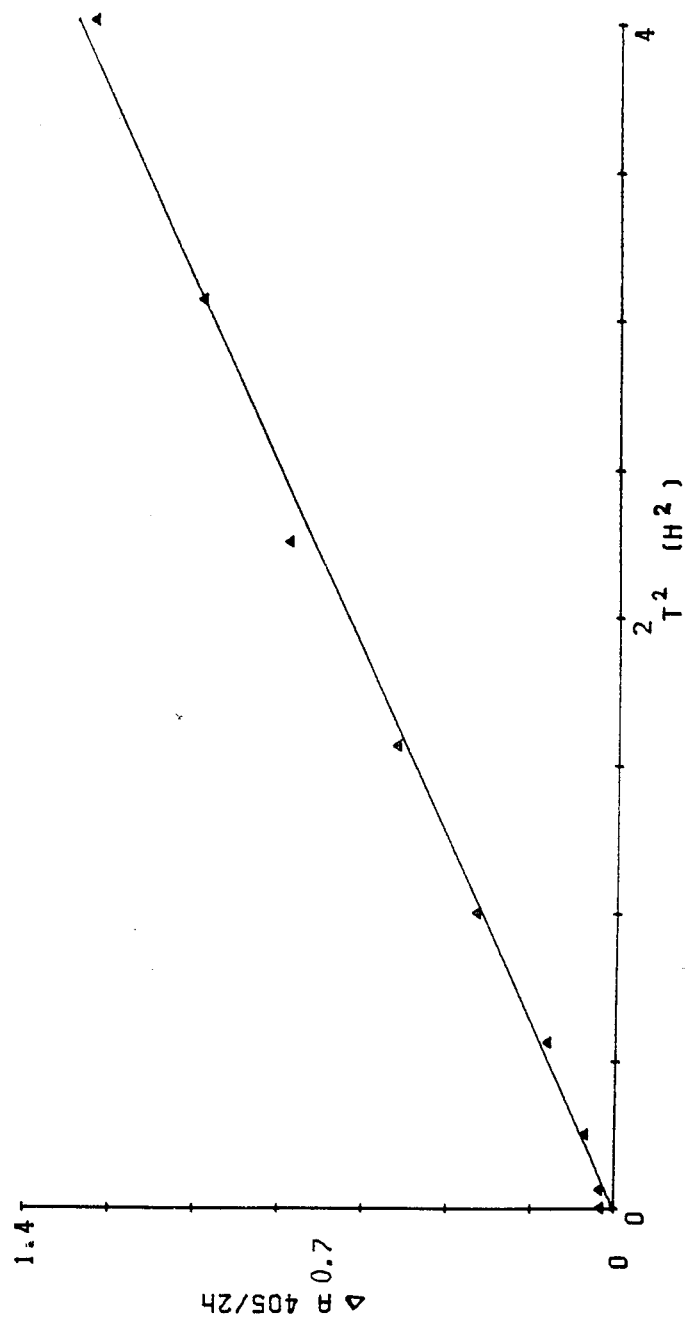

In the reaction underlying the present assay method the formation of p-nitroaniline, measured as a change in optical density, is approximately proportional to the square of time, when certain conditions are met with. This is called a parabolic system. In FIG. 3 the change of the optical density is plotted against the square of time in hours. This shows the substantially linear relation.

Figure 4A:
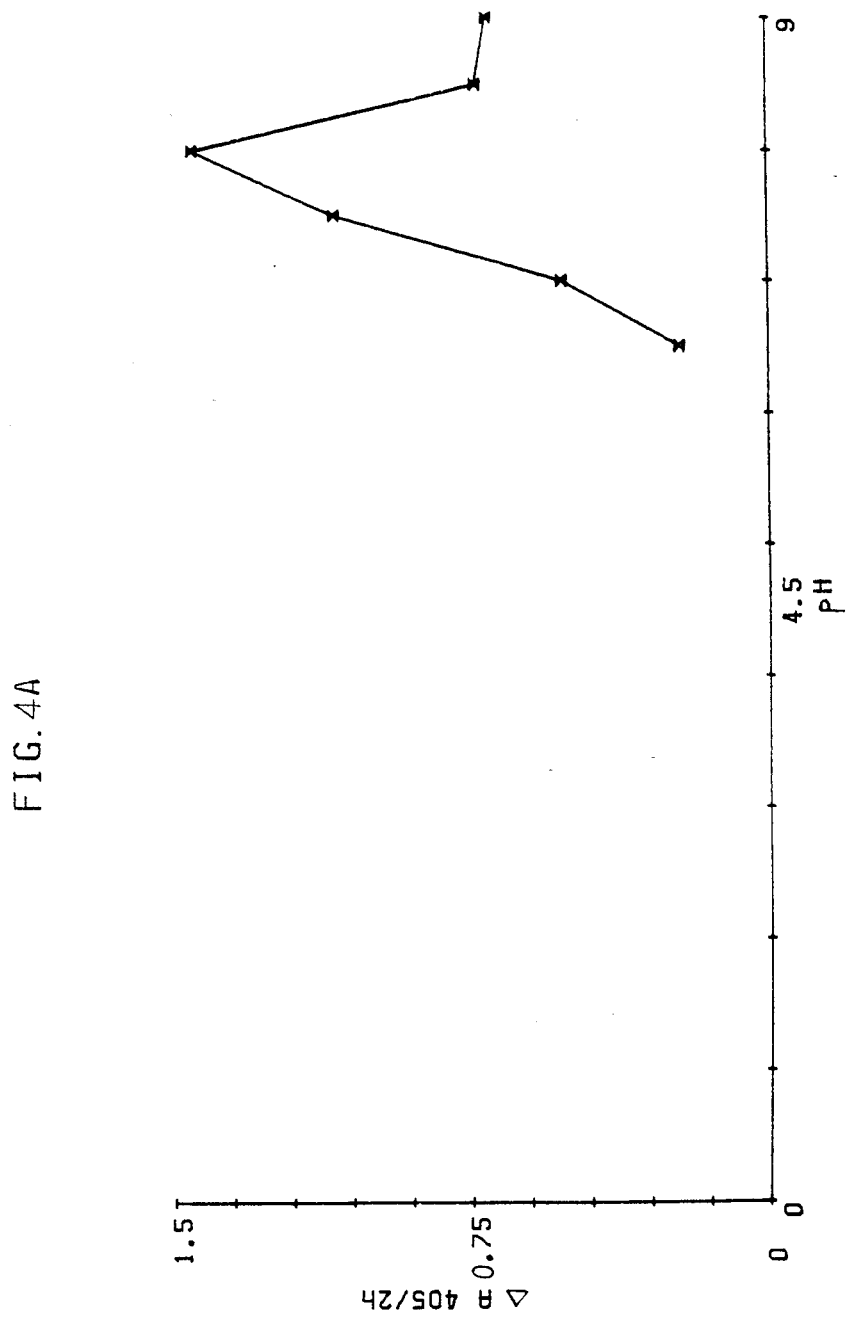

The present system is dependent on the pH (see FIG. 4A). The optimum lies at a value of 8, but different pH-values may be selected, for example the more physiological pH of 7.5, in order to simplify the measurements in biological fluids.

Figure 4B:
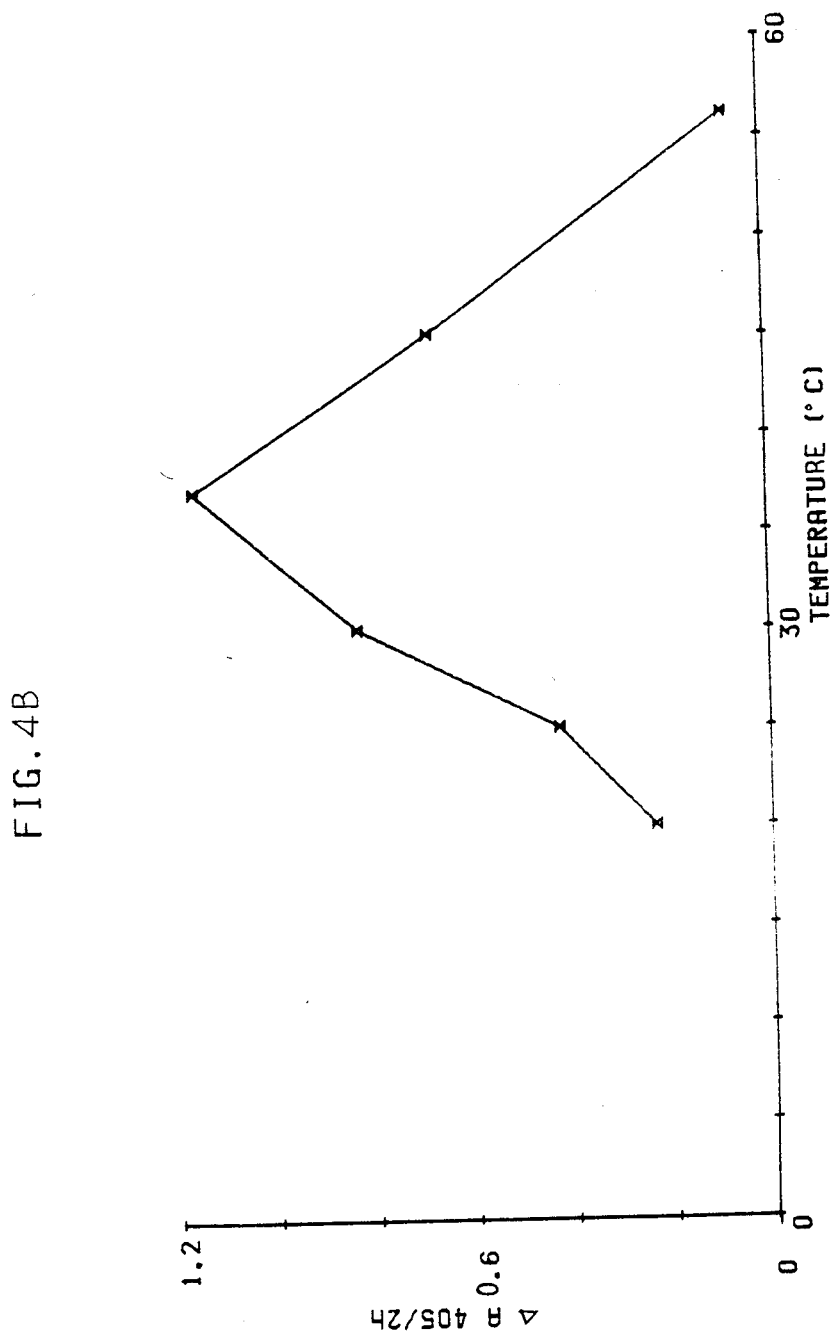

The system shows a temperature optimum of about 37° C. (FIG. 4B). Lower temperatures may be used as well, however, for example 25° C., so as to avoid evaporation during long incubations.

Although, on variation of the plasminogen concentration (FIG. 5) a plateau is reached at a plasminogen concentration of about 0.06–0.07 µM it is preferred to use somewhat higher plasminogen concentrations so as to minimize test result variations due to small differences in plasminogen concentration. Good results have been obtained with a plasminogen concentration of 0.13 µM.

Generally, the incubation time need not be longer than 2 hours. In case a higher sensitivity is necessary for assaying very small amounts of the activator (TA) the incubation may be performed during a longer period of time, however. The maximum sensitivity and the detection limit are limited, however, by the presence of traces of plasmin in the plasminogen preparation.

Figure 6A:
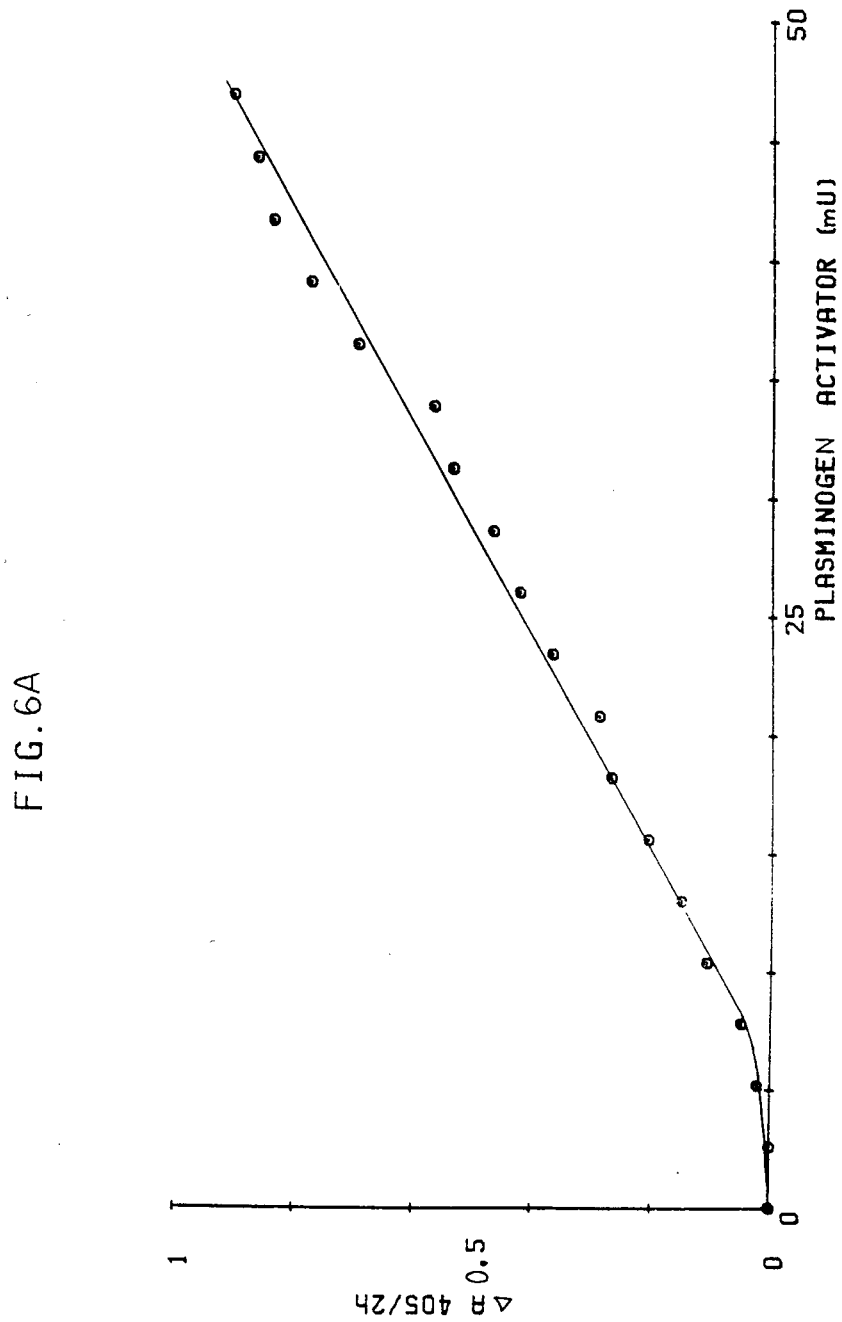
Figure 6B:
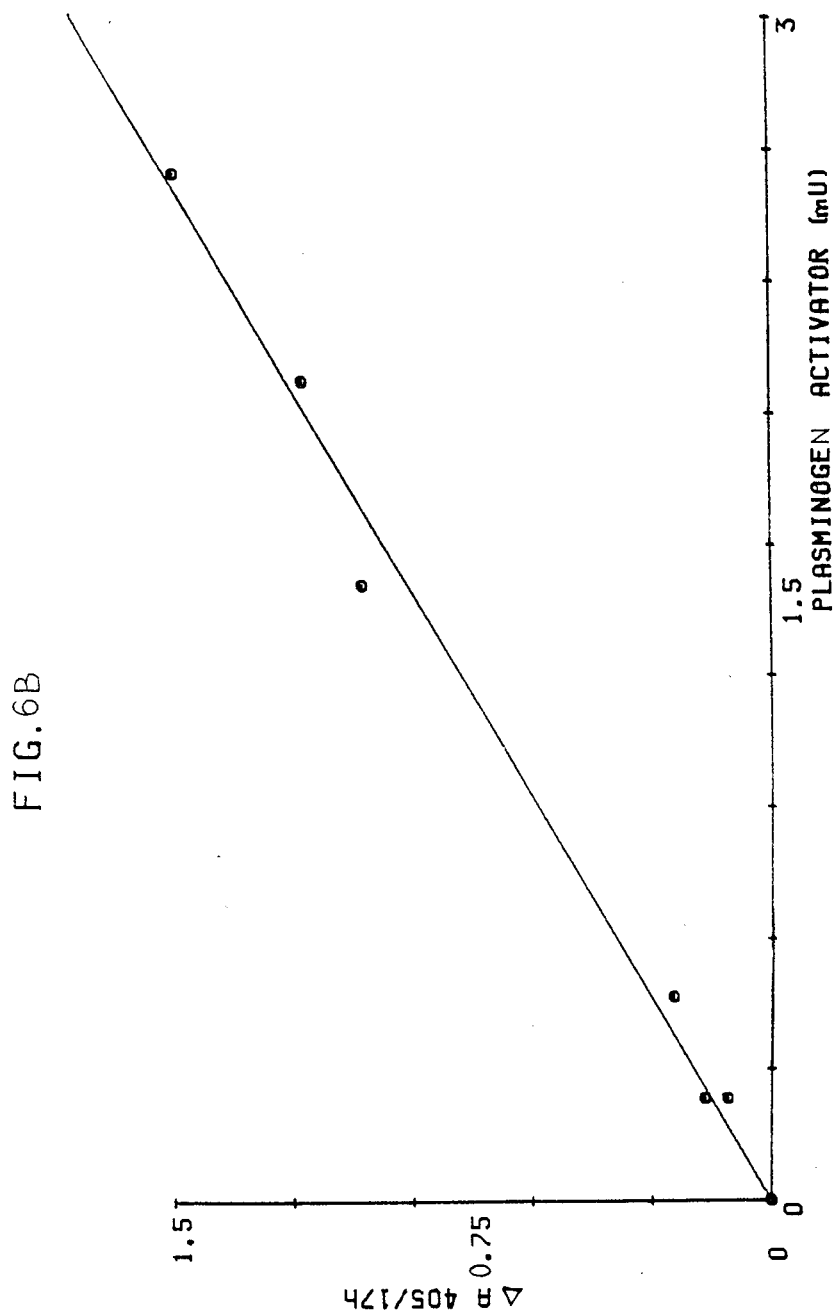

When working under standard conditions the change of the optical density at 405 nm after a certain incubation time is directly proportional to the activator concentration. Thus FIG. 6A illustrates a standard curve of the optical density change at 405 nm after 2 hours of incubation against the concentration of added purified TA. In FIG. 6B the standard curve after 17 hours of incubation is given. In both cases the linearity is excellent over a wide range.

The present spectrophotometric assay method has been compared with the known fibrin plate method. The correlation between both of the methods is good. The sensitivity and the accuracy of the present method is better than that of the fibrin plate method, however. The great advantage of the present method is, however, its simplicity and the short period of time necessary for obtaining the results. The fibrin plate method requires 17 hours, whereas the results of the present method can be known in 1 to 2 hours. In view of this, the present method is also suitable for checking the purity of TA preparations so as to determine the progress of purification operations. In that case it is often sufficient to detect qualitatively the presence or absence of TA. Dependent on the TA activity of the sample the results are then known in 2 to 10 minutes. The present assay method is sufficiently specific to detect exclusively TA even if the preparation is impure.

The present method can be used for assaying the TA activity in plasma. The present method appears to be very specific, also in the assay of TA in plasma. Namely, when anti-TA-IgG was added, almost no TA appeared to be detectable. This shows that even in the presence of other proteolytic enzymes in the plasma these enzymes are not assayed with the present assay system.

It was found that the assay of very low TA activities in plasma is strongly influenced by the presence of inhibitors, probably $\alpha_2$-antiplasmin and $\alpha_2$-macroglobulin. For the assay of low TA activities in plasma it is necessary to remove or to inactivate these inhibitors, for example by performing the assays with euglobulin fractions. Also in the assays with euglobulin fractions a good correlation between the present method and the fibrin plate method could be found.

The fibrin or fibrinogen fragments used as a stimulator in the present assay method have a specificity for TA, as the plasminogen activator urokinase is not stimulated.

The present method needs less time and is more sensitive than the fibrin plate or clot lysis time methods. Also, the present method, in contrast with other methods, is suitable for kinetic experiments of the plasminogen activation by TA. All of the reagents used are soluble, and the test is easy to perform and requires no special equipment.

For routine measurements of large numbers of samples the assay can be carried out in microtiter plates, and a special multichannel spectrophotometer can be used with only small loss in accuracy.

The incubation can be performed at 37° C. instead of 25° C., when properly closed tubes are used to prevent evaporation. This accelerates the reaction rate by a factor of about 3.

When turbid samples have to be assayed the reproducibility can be increased by measuring at various incubation times and to take as a measure for the activity the slope of the $\Delta A$ (change of the optical density) against the time squared instead of $\Delta A$ after a fixed period of time. Measurements after various incubation times may be performed easily with the microtiter plate and a suitable microtiter spectrophotometer.

Another use of the present method is the analysis of the activity of the tissue type activator in tissue and cell-culture media. As the fibrinogen fragments have no influence on the activity of urokinase (UK), it is possible to distinguish between TA and UK by assaying in the presence and in the absence of the stimulator. If, however, both UK and TA are present simultaneously and the amount of UK is much larger than the amount of TA, measurements in the absence and presence of stimulator does not solve the problem. In that case measurements in the presence and in the absence of anti-UK-IgG and anti-TA-IgG will give the desired result.

The invention also relates to a combination of the kit-type for effecting the above-described assay method. Such a combination comprises at least the following components:

a. a container with a measured amount of a substrate for plasmin giving a detectable reaction product on reaction with plasmin, especially H-D-Val-Leu-Lys-pNA;

b. a container with a measured amount of plasminogen, and c. a container with a measured amount of water-soluble fibrinogen or fibrin fragments comprising at least partially the D-domains of the fibrinogen or fibrin molecule and being smaller than fragment X, preferably fibrinogen or fibrin fragments obtained by reacting fibrinogen or fibrin with CNBr, removing the lower molecular components from the reaction product and lyophilizing the solution obtained.

A preferred kit according to the invention comprises containers with the preferred substrate for plasmin, plasminogen, and the preferred lyophilized fibrinogen fragments in a weight ratio of 12–20:1:10–20, especially of 14–15:1:10.

The kits according to the invention may also comprise a container with a buffer solution, optionally containing a surfactant, preferably Tween 80. Preferably, the buffer solution is a 0.1M Tris-HCl buffer having a pH of 7.5.

Optionally, the kits according to the invention comprise one or more operating instructions, for example an instruction as described in the following example XI.

On the other hand, a kit according to the invention may also comprise a container with a measured amount of tissue type plasminogen activator (TA) so as to allow control measurements.

Also, the kits according to the invention may comprise containers with measured amounts of anti-TA-IgG and anti-UK-IgG.

The following examples illustrate the invention.

EXAMPLE I

Preparation of the stimulator

Lyophilized human fibrinogen (1 g; Kabi; grade L) is dissolved in 100 ml of 70% (v/v) formic acid. Then 1.3 g CNBr is added and the mixture is left for 24 hours at room temperature. Then the solution obtained is dialysed against 4×2 liters of distilled water for 16–24 hours at room temperature. Lyophilization of the solution yields about 700 mg of fibrinogen fragments which may be used as a stimulator in the present assay method.

In the following examples the following materials are used:

Plasminogen. Human plasminogen, a mixture mainly consisting of lys-plasminogen isolated from fraction III according to Cohn by means of affinity chromatography on lysine-eupergit.

Plasminogen activator. This was isolated from human uteri by means of the method of Rijken et al. [Biochim. Biophys. Acta 580 (979), 140–153].

Chromogenic plasmin substrate. This substrate has the formula H-D-Val-Leu-Lys-p-nitroanilide.2HCl and was obtained from the firm Kabi.

EXAMPLE II

Plasminogen activator (TA; 0.052 IE) is incubated at 25° C. in 1 ml of Tris-HCl buffer (0.10M, pH 7.5) containing 0.13 $\mu$M of plasminogen, 0.1% (v/v) Tween 80, and 0.30 mM chromogenic plasmin substrate. The incubation is carried out in the presence of various amounts of fibrinogen fragments obtained according to example I, and the optical density at 405 nm after 2 hours is compared with the optical density of mixtures obtained in parallel tests in which no activator is used.

Figure 2:
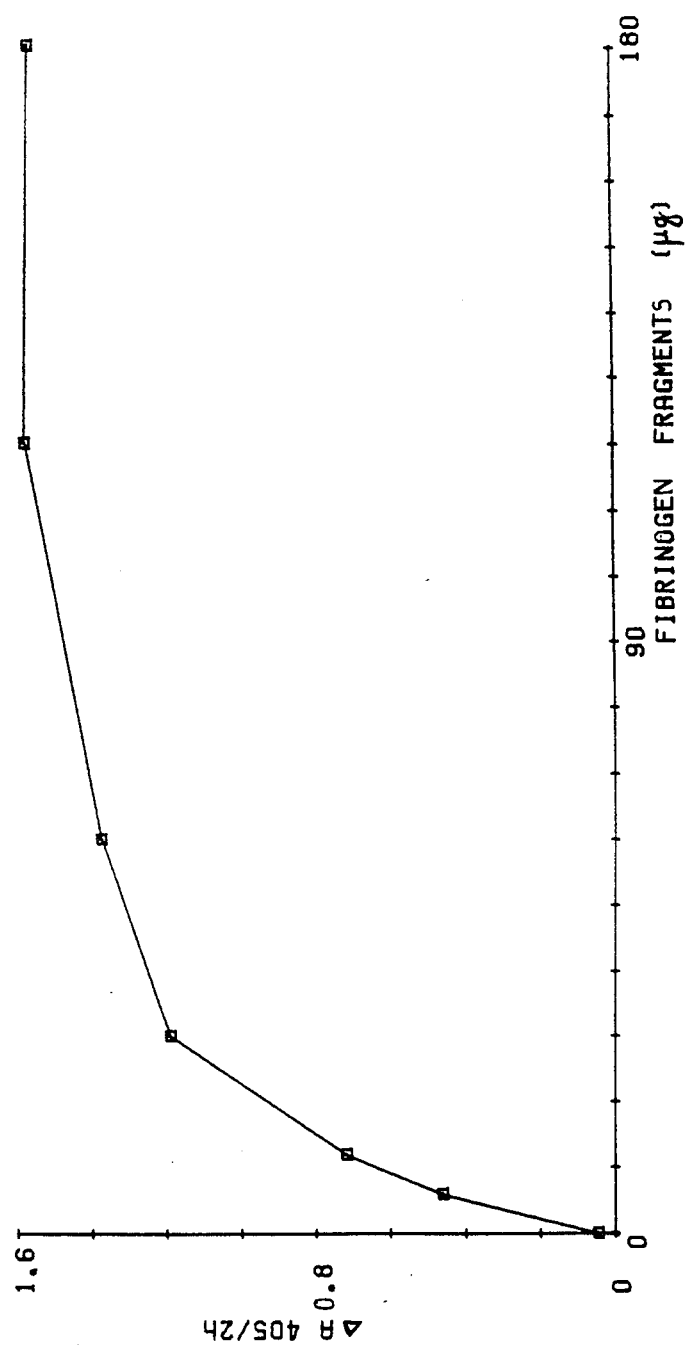

The results are given in FIG. 2 in which the change of the optical density ($\Delta A(405)/2h$) is plotted against the amount of added fibrinogen fragments. FIG. 2 shows that the maximum change of the optical density is reached at an amount of fibrinogen fragments of about 120 $\mu$g.

EXAMPLE III

Plasminogen activator (0.052 IE) is incubated at 25° C. in 1 ml of Tris-HCl buffer (0.10M, pH 7.5) containing 0.13 μM of plasminogen, 0.1% (v/v) of Tween 80, 0.12 mg/ml of fibrinogen fragments and 0.30 mM of chromogenic plasmin substrate. The optical density at 405 nm after various incubation times is measured and simultaneous control tests are carried out without activator. In FIG. 3 the difference in optical density between corresponding tests with and without activator is plotted against the square of the incubation time. FIG. 3 shows that there is a fair linearity between these values.

EXAMPLE IV (A) Plasminogen activator (0.052 IE) is incubated at 25° C. in 1 ml of Tris-HCl buffer (0.10M) of varying pH. The concentrations of plasminogen, chromogenic plasmin substrate and fibrinogen fragments are the same as in example III. Blanks are run at each of the pH-values tested. FIG. 4A shows the change of the optical density at 405 nm after 2 hours plotted against the pH-value. The optimum lies at about pH=8.

(B) The tests described in example III are carried out at various temperatures. Blanks are run at each temperature. The results are given in FIG. 4B. The temperature optimum lies at about 37° C.

EXAMPLE V

The tests described in example III are carried out, but the plasminogen concentration is varied. Simultaneous blanks are run at each of the plasminogen concentrations. In FIG. 5 the changes of the optical density after 2 hours of incubation are plotted against the plasminogen concentration in μM. FIG. 5 shows that a plateau is reached at a plasminogen concentration of about 0.07 μM.

EXAMPLE VI (A) The test is carried out under the conditions described in example III, but the amount of plasminogen activator is varied. FIG. 6A shows that, in a broad concentration range, there is a linear relationship between the change of the optical density after 2 hours of incubation and the concentration of the plasminogen activator.

(B) The test is carried out as under (A), but the optical density is measured after 17 hours of incubation. Moreover 0.1% (w/v) of gelatin is added to the buffer. FIG. 6B shows that good linearity is obtained here as well.

EXAMPLE VII

The results obtained with the present method are compared with those obtained with the fibrin plate method by assaying various amounts of plasminogen activator both with the present method and with the fibrin plate method. The present method is carried out as described in example III, but the measurement is carried out after 4 hours of incubation. The fibrin plate method is carried out as described by Haverkate et al. in "Progress in chemical Fibrinolysis and Thrombolysis" Vol. 1 (1975), page 151–159 (Raven Press, New York). Incubation is effected during 18 hours at 37° C.

Figure 7:
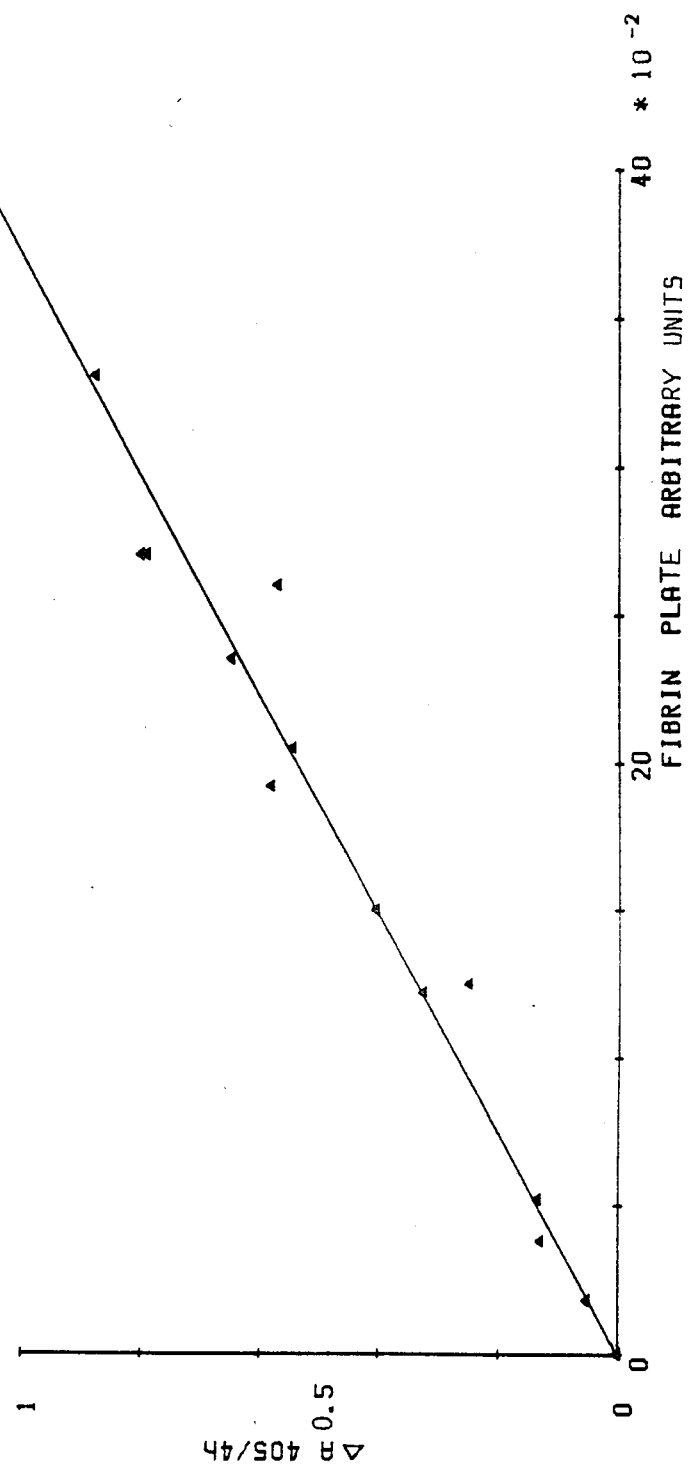

FIG. 7 shows that there is a good correlation between the methods.

EXAMPLE VIII

Figure 8:
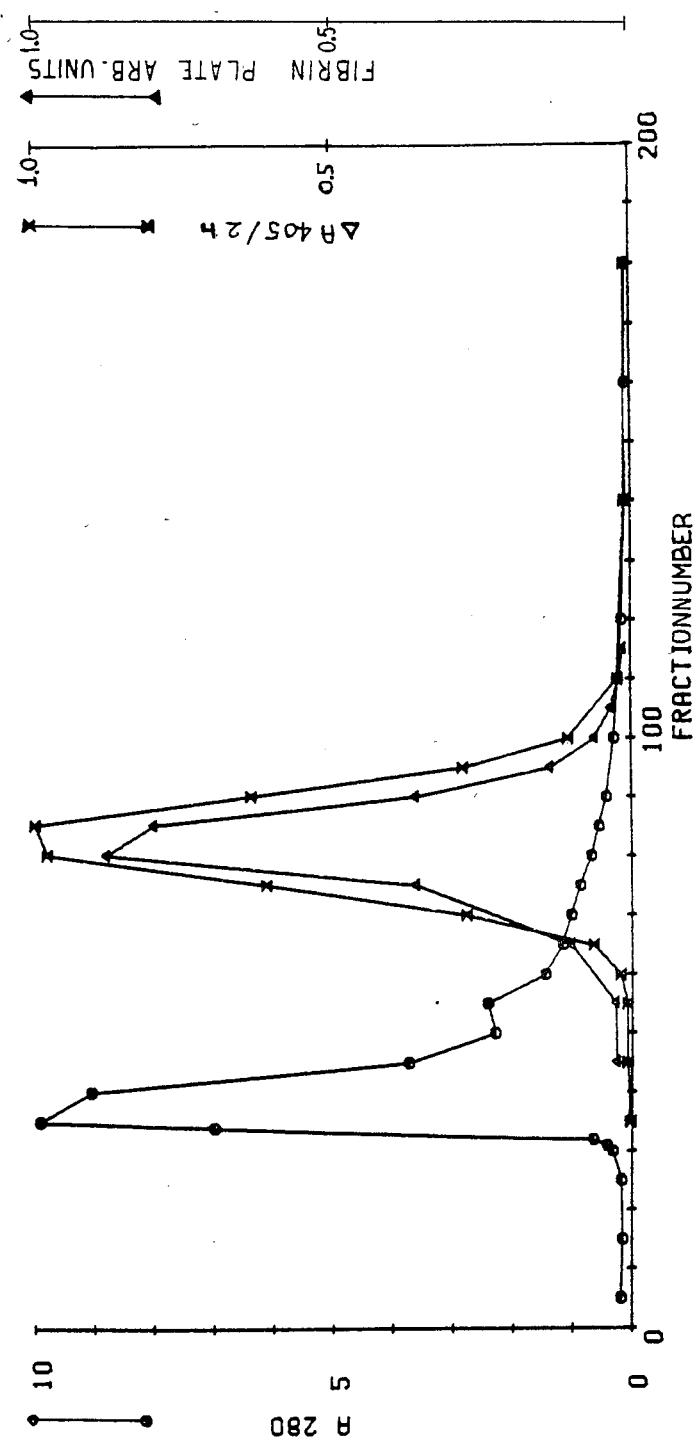

An extract of human uteri is purified by chromatography on zinc chelate/sepharose by means of the method described by Rijken et al. (see above). Samples of 5 μl of each of the fractions are assayed for TA-activity by means of the present method (example III) and according to the fibrin plate method. Again, FIG. 8 shows a good correlation between the methods.

EXAMPLE IX

Plasma (0.10 ml) of a person treated previously with DDAVP (this treatment serves to increase the TA concentration in the plasma) is incubated in 0.4 ml of Tris-HCl buffer (0.1M, pH 7.5) containing 0.1% (v/v) of Tween 80 and various amounts of anti-TA-rabbit-IgG for 30 minutes. Then, the chromogenic plasmin substrate, the fibrinogen fragments and the plasminogen are added according to example III and the residual activity of the plasminogen activator is assayed by incubation according to the procedure of example III for 2 hours. The change of the optical density was measured in comparison with parallel tests with normal blood plasma.

Figure 9:
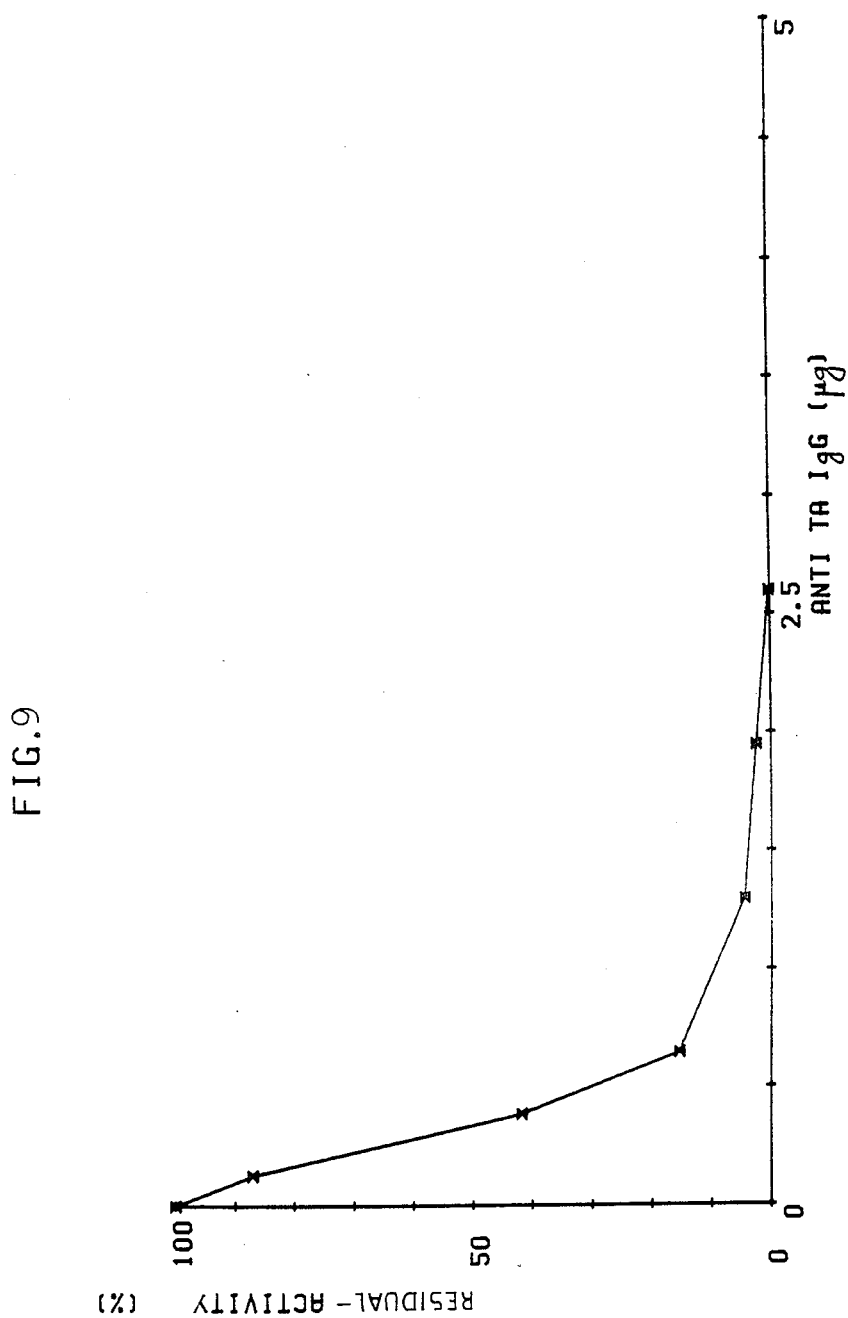

In FIG. 9 the percentage of residual activity is plotted against the anti-TA-IgG concentration. This shows that the present assay method is specific for TA.

EXAMPLE X

Figure 10:
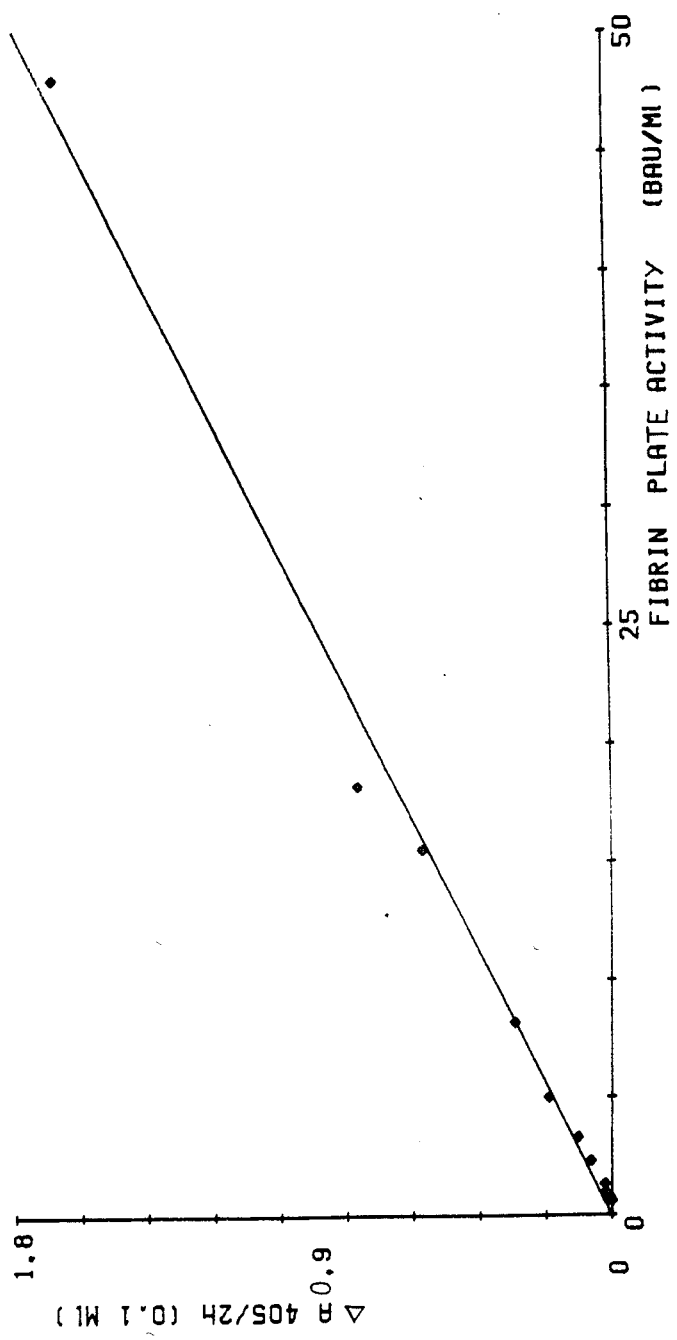

Euglobulin fractions are prepared according to the method of Kluft [Thrombos. Haemostas. 41 (1979), 363–383 and "Progress in Fibrinolysis" (1981) 24–30; Churchill Livingstone, Edinburgh]. Fractions (0.10 ml) are assayed by the method according to example III and also (0.03 ml) by the fibrin plate method also described by Kluft. In FIG. 10 the results of the present method are plotted against the results obtained with the fibrin plate method (arbitrary units). Again, there is a good correlation between the methods. FIG. 10A shows the first part of the graph of FIG. 10 in enlarged form. The correlation appears to be excellent, also with low TA activities.

EXAMPLE XI

Standard procedure

A. A test tube is charged with (0.48-v) ml of Tris-HCl buffer, pH 7.5 containing 0.1% (v/v) of Tween 80. A solution of fibrinogen fragments in distilled water (0.02 ml; 6 mg/ml) is added and mixed carefully. Then v ml of a sample to be assayed for plasminogen activator activity is added (5–55 mIE; $v \leq 0.1$ ml). After careful mixing, 0.40 ml of a 0.75mM solution of D-Val-Leu-Lys-pNA in the above-mentioned Tris buffer is added. Finally, the reaction is initiated by addition of 0.10 ml of a 1.3 μM plasminogen solution in the same Tris buffer. After 2 h of incubation at 25° C. the optical density at 405 nm is measured against distilled water. Simultaneous blanks are carried out in which v ml of Tris buffer instead of plasminogen activator solution is added. The difference in optical density between corresponding assays with and without plasminogen activator shows an almost linear dependency on the amount of active plasminogen activator in the sample.

B. The standard procedure described under A. also may be carried out in microtiter plates of colourless plastic. In that case the assay is carried out under the conditions described, but only ¼ of the volumes mentioned are used. The optical density at 405 nm after 2 h of incubation is measured with a special multichannel spectrophotometer.

EXAMPLE XII

A kit for 25 assays according to example XIA or for 100 assays according to example XIB comprises the following:
- a container with 15 ml of sterile 0.1M Tris-HCl buffer, pH 7.5 containing 0.1% (v/v) of Tween 80,
- a container with 7.5 μmoles of H-D-Val-Leu-Lys-pNA in dry form, to which 10 ml of Tris buffer has to be added before use,
- a container with 0.3 mg of plasminogen in dry form, to which 2.5 ml of Tris buffer has to be added before use,
- a container with 3 mg of fibrinogen fragments prepared according to example I in dry form, to which 0.5 ml of distilled water has to be added before use,
- an operating instruction according to examples XIA and XIB and
- an instruction for the preparation of euglobulin fractions according to the method of Kluft (see above).

EXAMPLE XIII

A further kit comprises the same components as that of example XII, but additionally comprises a container with 0.5 IE of plasminogen activator (TA) in about 0.10 ml of sterile Tris buffer, for effecting control measurements.

EXAMPLE XIV

A third kit comprises the components of the kits of example XII or of example XIII, but additionally comprises containers with suitable amounts of freeze-dried immunoglobulin against TA and UK, together with corresponding operating instructions.

We claim:

1. In a process for assaying the activity of tissue plasminogen activator in a sample, comprising the incubation of the sample with:
   (a) plasminogen,
   (b) a stimulator for the conversion of plasminogen to plasmin by tissue plasminogen activator, and
   (c) a substrate for plasmin which gives a detectable reaction product on reaction with plasmin;
followed by a step of measuring the amount of reaction product formed, the improvement comprising using, as the stimulator (b), water-soluble fibrinogen or fibrin fragments comprising at least partially the D-domains of the fibrinogen or fibrin molecule and being smaller than fragment X.

2. The process of claim 1, wherein the fibrinogen or fibrin fragments have been obtained by reacting fibrinogen or fibrin with CNBr and removing the lower molecular weight components from the reaction product.

3. A kit for assaying the activity of tissue plasminogen activator in a sample, comprising:
   (a) a container with a measured amount of a substrate for plasmin giving a detectable reaction product on reaction with plasmin,
   (b) a container with a measured amount of plasminogen, and
   (c) a container with a measured amount of water soluble fibrinogen or fibrin fragments comprising at least partially the D-domains of the fibrinogen or fibrin molecule and being smaller than fragment X.

4. A kit according to claim 3, wherein the substrate for plasmin is H-D-Val-Leu-Lys-p-NA.

5. A kit according to claim 3, wherein the fibrinogen or fibrin fragments have been obtained by reaction of fibrinogen or fibrin with CNBr, removal of the lower molecular weight components from the reaction product, and lyophilization of the solution obtained.

6. A kit according to claim 3, wherein the substrate for plasmin is H-D-Val-Leu-Lys-p-NA, and the fibrinogen or fibrin fragments have been obtained by reaction of fibrinogen or fibrin with CNBr, removal of the lower molecular weight components from the reaction product and lyophilization of the solution obtained.

7. A kit according to claim 6, wherein the weight ratio of H-D-Val-Leu-Lys-p-NA to plasminogen to fibrinogen fragments is 12–20:1:10–20.

8. A kit according to claim 6, wherein the weight ratio of H-D-Val-Leu-Lys-p-NA to plasminogen to fibrinogen fragments is 14–15:1:10.

9. A kit according to claim 3, additionally comprising a container with a buffer solution optionally containing a surfactant.

10. A kit according to claim 3, wherein the buffer solution is 0.1M Tris-HCl buffer pH 7.5.

11. A kit according to claim 9, wherein the surfactant is Tween 80.

12. A kit according to claim 9, wherein the buffer solution is 0.1M Tris-HCl buffer pH 7.5, and the surfactant is Tween 80.

13. A kit according to claim 3, additionally comprising a container with a measured amount of tissue plasminogen activator.

14. A kit according to claim 3, additionally comprising measured amounts of anti-TA-IgG and anti-UK-IgG in separate containers.

* * * * *

UNITED STATES PATENT AND TRADEMARK OFFICE
CERTIFICATE OF CORRECTION

PATENT NO. : 4,563,420

DATED : Jan. 7, 1986

INVENTOR(S) : Verheijen et al.

Page 1 of 2

It is certified that error appears in the above-identified patent and that said Letters Patent is hereby corrected as shown below:

First page, following 3rd line of 2nd col., insert:

--FOREIGN PATENT DOCUMENTS 76 07433   1/1977    Netherlands
77 05891   11/1977   Netherlands

OTHER PUBLICATIONS

NATURE, Vol. 218, April 13, 1968, B. Blomback et al.: "N-Terminal Disulphide Knot of Human Fibrinogen," pp. 130-134

CHEMICAL ABSTRACTS, Vol. 97, No. 11, Sept. 13, 1982, p. 538, Abstract No. 97:89640g CHEMICAL ABSTRACTS, Vol. 89, No. 23, Dec. 4, 1978, p. 390, Abstract No. 89:194613h CLINICAL CHEMISTRY, Vol. 28, No. 5, May 1982, Campbell E.E. et al.: "A Colorimetric Assay for Releasable Plasminogen Activator" pp. 1125-1128

M. Ranby and P. Wallen: "A Sensitive Parabolic Rate Assay for the Tissue Plasminogen Activator," Progress in Fibrinolysis, Vol. V (1981), pp. 233-235

F. Haverkate et al.: "Protective Effect of Calcium in the Plasmin Degradation of Fibrinogen and Fibrin Fragments D", Thrombosis Research, Vol. 10, 1977, pp. 803-812

W. Nieuwenhuizen et al.: "Factors Influencing the Structure of Terminal Plasmin Degradation Products of Human Fibrinogen and Fibrin", Biochimica et Biophysica Acta, 667, (1981) pp. 321-327.

S. V. Pizzo et al.: "Subunit Structure of Fragment D from Fibrinogen and Cross-Linked Fibrin", The Journal of Biological

UNITED STATES PATENT AND TRADEMARK OFFICE
CERTIFICATE OF CORRECTION

PATENT NO. : 4,563,420  
DATED : Jan. 7, 1986  
INVENTOR(S) : Verheijen et al.

Page 2 of 2

It is certified that error appears in the above-identified patent and that said Letters Patent is hereby corrected as shown below:

Chemistry, Vol. 248, (1973), pp. 4584-4590

D.C. Rijken et al.: "Purification and Partial Characterization of Plasminogen Activator from Human Uterine Tissue," Biochimica et Biophysica Acta, 580, (1979), pp. 140-153

F. Haverkate et al.: "Fibrin Plate Assay", Progress in Chemical Fibrinolysis and Thrombolysis, Vol. 1. (1975), pp. 151-159

C. Kluft: "Studies on the Fibrinolytic System in Human Plasma: Quantitative Determination of Plasminogen Activators and Pro-activators", Thrombos. Haemostas., 41, (1979), pp. 365-383

C. Kluft: "Quantitation and Behaviour of Extrinsic or Vascular Plasminogen Activator in Blood", Progress in Fibrinolysis, (1981), pp. 24-30--.

Col. 6, line 44, "(979)" should read --(1979)--; and

Col. 10, line 38, "claim 3" should read --claim 9--.

Signed and Sealed this

Twenty-eighth Day of October, 1986

[SEAL]

Attest:

DONALD J. QUIGG

Attesting Officer  Commissioner of Patents and Trademarks